(12) United States Patent
Sferrazza

(10) Patent No.: US 9,003,693 B2
(45) Date of Patent: Apr. 14, 2015

(54) CONTROL OF ZEBRA MUSSELS IN CLOSED SERVICE WATER SYSTEMS

(71) Applicant: ASI Group Ltd., St. Catharines (CA)

(72) Inventor: Carmelo Sferrazza, Fonthill (CA)

(73) Assignee: ASI Group Ltd., St. Catharines, ON (CA)

(*) Notice: Subject to any disclaimer, the term of this patent is extended or adjusted under 35 U.S.C. 154(b) by 81 days.

(21) Appl. No.: 13/756,111

(22) Filed: Jan. 31, 2013

(65) Prior Publication Data

US 2014/0208635 A1 Jul. 31, 2014

(51) Int. Cl.
*A01M 1/24* (2006.01)
*C02F 1/50* (2006.01)
*A01N 59/08* (2006.01)
*C02F 1/00* (2006.01)

(52) U.S. Cl.
CPC . *C02F 1/50* (2013.01); *A01N 59/08* (2013.01); *C02F 1/008* (2013.01); *C02F 2209/001* (2013.01); *C02F 2209/36* (2013.01); *C02F 2303/20* (2013.01)

(58) Field of Classification Search
USPC ............. 43/124; 210/754, 755, 753, 756, 739
See application file for complete search history.

(56) References Cited

U.S. PATENT DOCUMENTS 5,256,310 A * 10/1993 Brooks ....................... 210/747.5
5,442,967 A * 8/1995 McClane .................... 73/863.22

FOREIGN PATENT DOCUMENTS

CA 2091928 10/1993
CA 2230582 3/1997

OTHER PUBLICATIONS

"Eradication and Control Tactics: Chemical Application" pp. 5-7, Carolynn Culver et al., Jan. 2006.*
Boelman, S.F. et al., Zebra Mussel (*Dreissena polymorpha*) Control Handbook for Facility Operators, First Edition, US Army Corps of Engineers—Waterways Experiment Station, Miscellaneous Paper EL-97-1, Jun. 1997.
Claudia, R. and Mackie, G.L. "Practical Manual for Zebra Mussels Monitoring and Control." CRC Press (Boca Raton, Florida), 1994, pp. 108-109.
Wilcox, S.J. and Dietz, T.H. "Potassium Transport in the Freshwater Bivalve *Dreissena polyrnorpha*." J. Exp. Biol. 198, 1995, pp. 861-868.
Duran et al. "Management strategies for the zebra mussel invasion in the Ebro River basin." Aquatic Invasions, 2010, vol. 5, Issue 3: 309-316.
Sprecher, S.L. and Getsinger, K.D. et al., "Zebra Mussel Research Program: Zebra Mussel Chemical Control Guide", US Army Corps of Engineers: Engineer Research and Development Center, Jan. 2000.

* cited by examiner

*Primary Examiner* — Christopher P Ellis
(74) *Attorney, Agent, or Firm* — Bereskin & Parr LLP/S.E.N.C.R.L., s.r.l.; Philip C. Mendes da Costa

(57) ABSTRACT

A method for controlling bivalve growth in a static or semi-static service water system of a plant is disclosed. Upon detecting an increase in the concentration of veligers or settlement stage bivalves, potassium is introduced into the service water to obtain a potassium cation concentration of between 10 mg/l and 150 mg/l for a period of 2 to 30 days. The methods are particularly useful for controlling zebra mussel growth in service water systems for fire prevention.

26 Claims, 1 Drawing Sheet

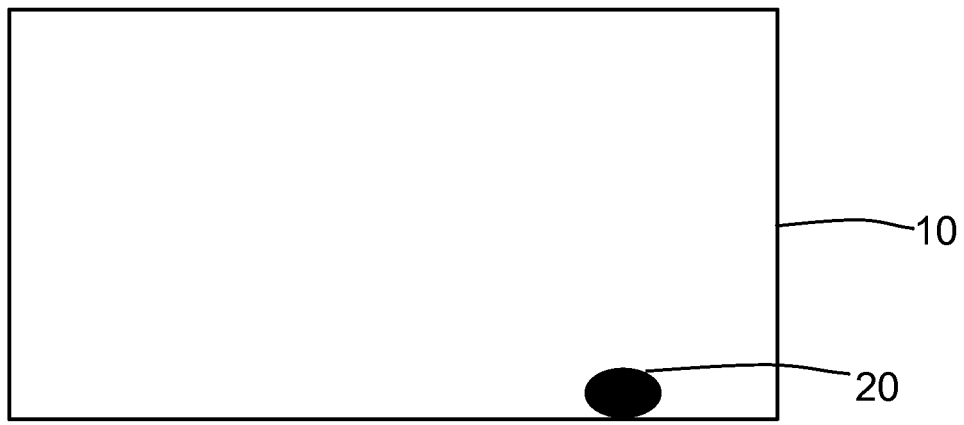

CONTROL OF ZEBRA MUSSELS IN CLOSED SERVICE WATER SYSTEMS

FIELD

The invention relates to methods for controlling bivalve growth in the service water system. More specifically, the invention relates to methods for controlling bivalve growth in a static or semi-static service water system using potassium cations.

BACKGROUND

The introduction of the zebra mussel (*Dreissena polymorpha*) to North America in 1986 has had a dramatic impact on water users throughout the continent. This organism has colonized the entire Great Lakes system, the Mississippi River and associated tributaries as well as inland waterways throughout North America. Another species of mussel, the quagga mussel (*Dreissena bugensis*) was introduced in the 1990's and has also spread throughout North America.

Although they are separate species they share a trait which has been devastating to raw water users throughout the continent. Mussel veligers (initial offspring) reach a stage in their maturation wherein they settle and attach themselves to hard surfaces. This is particularly troublesome for industrial water users as service water piping provides an ideal surface for attachment. Resulting problems include reduction of pipe bores and associated hydraulic carrying capacity, enhanced electro-corrosion of pipe materials and increased maintenance costs associated with the accumulation of shell debris. Since the early 1990's, industry has spent millions of dollars searching for mitigation methods which are reliable, cost effective and safe.

Mussel infestation is a particularly sensitive matter when considering water systems that are static or semi-static in nature, such as closed-loop cooling or fire protection systems. Fire protection piping at industrial facilities consists primarily of buried piping networks; although some contain sections of exposed piping. Distribution networks connect fire water supply pumps to fire protection outlets such as hydrants, automated sprinkler systems, and water spray/mist systems specifically designed for fire suppression during an emergency.

These systems are often characterized by low volumes of make-up water added continuously to maintain system pressure due to loss through leakage, or use through other purposes such as maintenance, washing, cooling, flushing or training. As a result, fresh, oxygenated water is sporadically introduced into the system replacing stagnant water. This exposes fire protection and other static and semi-static water systems to an increased risk of infestation by bivalves such as zebra mussels. In this way, mussels are able to colonize intermittent flow systems, become established, and proliferate as a result of sporadic infusions of fresh water. This poses a serious safety issue—even small numbers of mussels can cause problems in fire protection systems if they are flushed downstream during emergency use since, they can block or significantly reduce flow in the extremities of the distribution network (e.g., the narrower diameter piping and sprinkler nozzles).

Semi-static water systems have been difficult to effectively treat for mussel colonization using traditional methods, such as oxidants and specifically chlorination. Chlorination is non-selective and presents significant operational challenges in semi-static and static water systems mainly due to a characteristic of chlorine chemistry commonly known as "demand". Demand is the potential of a given water system to consume applied chlorine (via slime, algae, chemical reactions etc.) leaving little or no residual chlorine remaining to control the target species. In systems where the flow is intermittent, demand is a major factor which will render chlorination ineffective.

The only available option to overcome this problem is to constantly flow treated water through these systems so that the target chlorine residual can be replenished and maintained. When using chlorination for control, mussels generally need to be exposed to the chemical on a continuous basis for several weeks to achieve complete mortality and only under warm water conditions, e.g., >15° Celsius. Therefore, the volume of water required to be flushed through the system would be substantial and, in many cases, it is not practical for the industrial water user to use chlorination due to the large volumes of water involved. In addition, chlorination is even less attractive due to its high oxidation potential and associated risks including the production of undesired by-products, and the necessity for end-of-pipe treatment to mitigate environmental impacts and to comply with environmental regulations.

SUMMARY

In one aspect, there is provided a method for controlling bivalve growth in static or semi-static service water system by introducing potassium cations into the service water. The potassium cations may be introduced in the form of a potassium salt such as potassium chloride, or compounds or minerals with soluble potassium such as potash. Optionally, the potassium cations may be introduced in the form of potassium mono and divalent salts of phosphoric acid, potassium sulfate or sulfate of potash, or potassium bromide. In one embodiment, the potassium is introduced along with an oxidizer, such as in the form of potassium permanganate.

The methods described herein provide a number of advantages for the control of bivalves in service water systems. Potassium cations work by interfering with the bivalve's ability to transfer oxygen across the gill structure, resulting in asphyxiation. Bivalves affected by potassium cations typically exhibit paralysis symptoms, with their shell remaining open and non-responsive to stimulation. While potassium was originally considered with the expectation that its use could optimize the effects of oxidants (e.g. chlorine) in other chemical control programs, it has surprisingly been determined that potassium cations alone are highly effective, work faster than some oxidants, and at low levels exhibit a selective toxic effect against bivalves such as zebra mussels.

Furthermore, it has been determined that low concentrations of potassium are highly effective for both acute and chronic control of bivalves. Potassium concentrations of 30 mg/L were determined to be effective at preventing settlement of veligers, while concentrations of 40 mg/L were shown to result in up to 100% mortality of a target population within two weeks at water temperatures above 15° C. Remarkably, increasing the concentration to 100 mg/L resulted in 100% zebra mussel mortality in 48 hours at water temperatures above 15° C.

It has also been determined that treating the service water with potassium cations after an increase in the concentration of veligers and/or settlement stage bivalves is detected provides for the effective control of bivalve growth in service water systems. In particular, by targeting veligers and/or settlement stage bivalves such as pediveligers with potassium cations near the beginning and/or end of the reproductive cycle the need for continuous treatment spanning the entire reproductive period of the bivalves (approximately 6 months) is eliminated. Optionally, in one embodiment the methods described herein include two or more separate treatment periods. Preventing the settlement and/or translocation of veligers and settlement-stage mussels into a service water system, and not merely killing adult bivalves in the pipes, helps reduce the shell load within the service water system thereby preventing the accumulation of potentially dangerous debris. Surprisingly, the settlement and translocation of veligers and pediveligers can be inhibited at concentrations of potassium cation as low as 10 mg/l, preferably at least 20 mg/l and more preferably at least 40 mg/l. In one embodiment, the settlement and translocation of veligers and pediveligers can be inhibited at concentrations of potassium cation between 10 mg/l and 100 mg/l, preferably between 20 mg/l and 80 mg/l, and more preferably between 40 mg/l and 60 mg/l.

In one embodiment, the methods described herein are initiated towards the end of the bivalves' reproductive cycle. In one embodiment, the methods are initiated in response to an increase in concentration of pediveligers that occurs towards the end of the bivalves' reproductive cycle, typically in the fall. For example, in one embodiment, the methods described herein are initiated near or after the first appearance of pediveligers and/or settlement stage bivalves in the body of water, typically in late August to October. In one embodiment, a single yearly treatment towards the end of the bivalves' reproductive cycle is useful for the control of bivalves in static or semi-static service water systems. Initiating a treatment cycle towards the end of the bivalves' reproductive cycle after the appearance of pediveligers is particularly effective at eliminating the settlement of mussels within the service water system, killing newly settled mussels and preventing the accumulation of debris. In one embodiment, the methods described herein are initiated at the end or after the bivalves' reproductive cycle, such as between September and December. In one embodiment, the methods described herein are initiated only in spring after an increase in the concentration of veligers is detected. In one embodiment, the methods described herein are initiated only in fall after an increase in the concentration of settlement stage bivalves is detected.

In one aspect, the methods described herein may include two or more separate treatment periods. For example, in one embodiment the method involves a first treatment period in the spring near the start of the bivalves' reproductive cycle, and a second treatment period in the fall towards the end of the bivalves' reproductive cycle. In one embodiment, the method comprises a first treatment period after an increase in the number of veligers in the body of water or service water system in the spring and a second treatment period after an increase in the number of settlement stage bivalves and in particular pediveligers in the body of water or service water system in the fall.

The methods described herein also reduce or eliminate the majority of risks associated with the use of chlorine and other oxidizers for the control of bivalves in service water systems. Potassium cations do not normally bind to naturally occurring organic matter, and as such will maintain the target concentration over the course of the treatment period. The use of potassium cations at concentrations useful for the control of bivalves in water systems does not cause significant acute or chronic toxicity of standard testing organisms such as *Daphnia magna*, rainbow trout, *Cerodaphnia dubia* and fathead minnows. Treatment to reduce effluent toxicity is therefore rarely, if ever, required for most potassium cation treatment applications.

Other advantages of the methods described herein include the use of live specimen bioassays to determine the effectiveness of the treatment and prevent under or over treating the service water. The use of live specimen bioassays ensures that the amount of potassium cation introduced to service water system and the length of treatment is sufficient for controlling bivalve growth in various different service water systems and service water temperature conditions.

Accordingly, in one aspect there is provided a method for controlling bivalve growth in a static or semi-static service water system wherein service water is drawn occasionally from a body of water and introduced into the service water system. In one embodiment the method comprises:
   a. monitoring the body of water for the presence of veligers and/or pediveligers;
   b. when an increase in the concentration of veligers and/or settlement stage bivalves is detected, introducing potassium cations into the service water system to obtain a steady state potassium cation concentration of 10 to 150 mg/l; and
   c. maintaining the steady state concentration of potassium cation in the service water is maintained for at least 2 to 30 days.

In one embodiment, potassium cations are introduced into the service water system after an increase in the concentration of pediveligers is detected.

In another aspect there is provided a method for controlling bivalve growth in a static or semi-static service water system wherein service water is drawn occasionally from a body of water and introduced into the service water system comprising:
   a. introducing potassium cation into the service water of the service water system at a concentration sufficiently high to kill early stage bivalves and sufficiently low such that the early stage bivalves continue to respire and ingest potassium cations; and,
   b. maintaining the concentration of potassium cation in the service water of the service water system for 2 to 30 days.

In one embodiment, the method includes introducing potassium cation at a concentration sufficiently high to kill settlement stage bivalves.

In one embodiment, the methods described herein involve monitoring a live colony of the bivalves in the service water of the service water system or under potassium cation concentrations and temperatures comparable to those in the service water system and terminating treatment after the bivalves in the live colony die.

In one embodiment, the methods described herein for controlling bivalve growth are useful for preventing the settlement and/or translocation of veligers and settlement-stage mussels into a service water system In another embodiment, the methods described herein for controlling bivalve growth are useful for killing bivalves in the service water system. In one embodiment, the methods described herein are useful for both preventing the settlement and/or translocation of veligers and settlement-stage mussels as well as killing bivalves in the service water system, such as bivalves that are settled on a surface in the service water system. In a preferred embodiment, the methods described herein for controlling bivalve growth are initiated towards the end of the bivalves' reproductive cycle, such as after an increase in the concentration of pediveligers is detected in the body of water. Treatment of a service water system with potassium cations towards the end of the bivalves' reproductive cycle is particularly effective for preventing translocation and/or killing settlement-stage mussels. In one embodiment, the methods described herein are initiated in the fall, such as in late August to December. In one embodiment, the method is performed only in spring after an increase in the concentration of veligers is detected. In one embodiment, the method is performed only in the fall after an increase in the concentration of settlement stage bivalves is detected.

Optionally, the potassium cation may be introduced in the form of a potassium salt, such as potassium chloride. In one embodiment, the potassium chloride is aqueous potassium chloride.

In one embodiment, potassium cations are introduced into the service water of the service water system to obtain a steady state potassium cation concentration of greater than 100 mg/l, about 100 mg/l, between 20 to 100 mg/l, 20 to 80 mg/l, or between 40 and 60 mg/l such that the settlement of veligers and/or pediveligers within the service water system is inhibited and settlement stage bivalves are killed. Optionally, potassium cations are introduced into the service water of the service water system in two or more separate treatment periods.

In one embodiment, the methods described herein include flowing the service water through the service water system from an inlet to an outlet to obtain the desired concentration of potassium cation in the service water in the service water system and then terminating the flow of the service water. Optionally, the methods include analyzing the potassium cation concentration in the service water and increasing or decreasing the amount of potassium cation introduced into the service water in order to maintain the desired steady state concentration of potassium cations in the service water. In one embodiment, the method includes discharging service water from the service water system at the end of the treatment, such as to remove dead bivalves from the service water system.

In one embodiment, the methods described herein include assessing the effectiveness of the potassium cation for controlling bivalve growth in the service water system by seeding a water permeable container with a sample of live bivalves, placing the container in the service water or in water that has potassium cation concentrations and temperatures comparable to those in the service water system and determining the viability of bivalves in the container. In one embodiment, bivalve mortality is correlated with the effectiveness of the treatment. Optionally, bivalve mortality may be assessed by identifying at least one bivalve which is showing signs of potassium intoxication and removing it from the container, exposing the removed bivalve to untreated flowing water and classifying the bivalve as dead if the bivalve does not recover after at least 24 hours in the untreated water. In one embodiment, the bivalve is classified as dead if the bivalve does not recover after 48 hours in the untreated water.

It will be appreciated that each of the embodiments is optional and any aspect disclosed herein may be used with any one or more of the possible embodiments disclosed herein and accordingly the various embodiments may be used in any combination or sub-combination.

BRIEF DESCRIPTION OF THE DRAWINGS

FIG. 1 shows one embodiment of a water permeable container with a live colony of bivalves placed inside the container.

DETAILED DESCRIPTION

In one aspect, the present description provides a method for controlling bivalve growth in a static or semi-static service water system.

Static or semi-static service water systems contain a volume of service water that is available for uses such as cooling or fire protection (e.g., held in a storage tank or other reservoir). These service water systems often require low volumes of water to be added continuously or periodically to the system in order to compensate for loss and to maintain system pressure due to leakage or use of the service water for purposes such as maintenance, washing, cooling, flushing or training. Examples of static or semi-static service water systems include, but are not limited to, fire protection systems, closed-loop cooling systems, standpipes and intermittent supply industrial process water systems. Some static or semi-static service water systems are not designed to provide a continuous flow-through of service water from a water supply inlet to a water supply outlet but rather to provide a stand-by source of service water such as for fire prevention.

Static or semi-static service water systems occasionally draw service water from a body of water to fill, e.g., a storage tank in a service water system and/or maintain service water pressure due to leakage or discharge of the service water. Optionally, the water introduced into the static or semi-static service water may include water from a distributed water system such as city or county tap water. It will be appreciated that the method disclosed herein may be used in addition to any other treatment applied to water drawn from the body of water, such as any filtration or purification treatment that may be known in the art.

As used herein "body of water" refers to a body of water such as a natural or artificial lake, river, stream, well or reservoir that is capable of supporting the growth of bivalves. In a preferred embodiment, the volume of the body of water is significantly larger than the volume of the service water system.

As used herein, "bivalve" refers to a class of molluscs that have a laterally compressed body enclosed by a shell in two hinged parts. The methods described herein are particularly useful for the control of freshwater bivalves. In a preferred embodiment, the bivalves are mussels, optionally zebra mussels (*Dreissena polymorpha*) and/or quagga mussels (*Dreissena bugensis*).

As used herein "controlling bivalve growth" refers to preventing or inhibiting the settlement and/or colonization of bivalves and optionally includes killing the bivalves.

In one embodiment, the methods described herein include monitoring the body of water from which the service water is drawn and/or the service water for the presence of veligers and/or settlement stage bivalves such as pediveligers to determine if treatment is required. For example, in one embodiment, the methods described herein include monitoring the body of water from which the service water is drawn and/or the service water for the presence of settlement stage bivalves such as pediveligers so that treatment may commence when an increase in the concentration of settlement stage bivalves is detected. Optionally, 2 or more treatments may be initiated per year. In one embodiment, treatment may commence when an increase in veligers is detected in the spring. In one embodiment, treatment may commence during or after the latter stages of the yearly reproductive cycle. For example, in one embodiment, treatment is initiated after an increase in the concentration of pediveligers water system and/or the body of water. In one embodiment, treatment may commence when an increase in the concentration of early stage bivalves or settlement stage bivalves is detected. The presence of veligers, pediveligers, early stage bivalves and/or settlement stage mussels can readily be detected and monitored such as by visual inspection of water samples from the body of water or service water system, or by inspecting surfaces exposed to the body of water or service water system or by other methods known in the art. As used herein, visual inspection optionally includes the use of detection equipment that can be used to recognize the presence of veligers, pediveligers, early stage bivalves and/or settlement stage mussels such as a magnifying device such as a microscope, an image recognition system that analyzes images from a camera, or the like.

In one embodiment, the methods described herein are used when an increase in the concentration of veligers and/or settlement stage bivalves such as pediveligers is detected in the body of water or service water. Accordingly, in one embodiment, the body of water and/or service water is periodically monitored for the presence of veligers and/or settlement stage bivalves. In one embodiment, the body of water and/or service water is periodically monitored commencing near an expected start date of the reproductive cycle of the bivalve, such as when the water reaches a predetermined temperature in the spring which is indicative of the start date of the reproductive cycle. In one embodiment, the water is monitored in the spring and/or in the fall. In one embodiment, the body of water and/or service water is periodically monitored commencing near the expected first appearance of pediveligers in the body of water, typically in late August to October.

As used herein, "veligers" refers to the early stage planktonic form of zebra mussel larvae that develop directly from the egg stage. In one embodiment, the presence of veligers in water samples indicates that the reproductive cycle of zebra mussels has begun, and that settlement is about four to six weeks away. Veligers generally begin to appear in late May to early June or when water temperatures approach 8° Celsius or about 46° Fahrenheit. Veligers typically have a size range of typically about 60-150 µm. As used herein, the term "veliger" optionally includes post-veligers, which represent the second larval stage of the development of the zebra mussel and are typically about 150-200 µm.

As used herein, "settlement stage bivalves" refers to pediveligers, juveniles and/or adult mussels. Pediveligers are an intermediate stage between post-veligers and juveniles. Pediveligers have the ability to both swim and crawl (with a muscular foot). At this stage, pediveligers are actively seeking an ideal place to settle and will release and resettle frequently (called translocation). Pediveligers generally appear in late August to October and are typically about 200-300 µm. Juvenile mussels are a settled, non-reproductive form of zebra mussel that are often visible to the naked eye and have characteristic stripes. Juveniles generally being to appear in September to October and are typically 300 µm-5 mm. As used herein "early stage bivalves" refers to veligers, pediveligers and juvenile mussels.

In one embodiment, upon detection of an increase in the concentration of veligers or settlement stage bivalves, potassium cation is introduced into the service water of the service water system. By introducing potassium cation into the service water when an increase in the concentration of veligers and/or of settlement stage bivalves such as pediveligers is detected, the methods of the present invention allow for controlling bivalve growth without the need for continuous treatment of the service water.

A skilled person will appreciate that whether a treatment cycle should be initiated in response to a change in the concentration of veligers, pediveligers and/or settlement stage mussels will depend on the operational tolerance of a particular service water system. For example, small fluctuations in the level of pediveligers and/or settlement stage mussels may or may not represent an increase such that the introduction of potassium cations according to the methods described herein is warranted. In one embodiment, a treatment cycle is initiated after an increase in the concentration of veligers and/or settlement state bivalves in the body of water. In a preferred embodiment, a treatment cycle is initiated when an increase is the concentration of pediveligers is detected towards the end of the reproductive cycle and the potential settling of bivalves into the service water system. In one embodiment, a treatment cycle is initiated after a discharge of service water from the service water system, such that a large volume of service water is required to be drawn from the body of water and introduced into the service water system. In one embodiment, a treatment cycle may be initiated when there is concern that the levels of pediveligers and/or settlement stage mussels are increasing in the service water system or threatening the operation of the service water system. For example, in a preferred embodiment, a treatment cycle is initiated when an increase in the concentration of veligers and/or pediveligers is detected in the spring coinciding with start of the reproductive cycle of the bivalve, and a second treatment cycle is initiated in the fall coinciding with an increase in the concentration of pediveligers.

The inventors have also determined that maintaining a steady state potassium cation concentration between 10 and 150 mg/l or any range there between for 2 days to 30 days is surprisingly effective at controlling bivalve growth, killing bivalves and preventing undesirable infestations and buildup of bivalve shell debris within semi-static or static service water systems. In one embodiment, the methods described herein include introducing potassium cations in an amount sufficient to obtain a steady state potassium cation concentration of about 10 mg/l to 150 mg/l in the service water of the service water system, or any range there between. The amount of potassium cation may be sufficient to obtain a potassium cation concentration of about 10 mg/l, 20 mg/l, about 30 mg/l, about 40 mg/l, about 50 mg/l, about 60 mg/l, about 70 mg/l, about 80 mg/l, about 90 mg/l, about 100 mg/l, about 110 mg/l, about 120 mg/l, about 130 mg/l about 140 mg/l or about 150 mg/l.

In one embodiment, the inventors have determined that a target concentration of 100 mg/L of $K^+$ is the most effective application over a broad range of temperatures and flow conditions for the selective elimination of quagga and zebra mussels. Accordingly, in one embodiment, the range is preferably from 60-140 mg/l, more preferably from 80-120 mg/l and most preferably from 90-110 mg/l. In one embodiment, the potassium cation is introduced in an amount sufficient to prevent the settlement of veligers or pediveligers and/or kill settlement stage bivalves. As shown in Example 2, potassium cation concentrations of 20 mg/l to 40 mg/l inhibited the settling of veligers and early stage bivalves onto surfaces in a service water system. Inhibiting the settlement of veligers and early stage bivalves provides the advantage of reducing the amount of shell debris that may otherwise accumulate in a service water system. In one embodiment, the potassium cation is introduced in an amount between 10 mg/l and 100 mg/l, between 20 mg/l and 80 mg/l, or preferably between 40 and 60 mg/l. In one embodiment, the introduction of potassium cation in concentrations between 20 mg/l and 80 mg/l inhibits the settling of veligers and/or pediveligers.

In one embodiment, the methods disclosed herein include introducing potassium into the service water of the service water system at a concentration sufficiently high to kill early stage bivalves and sufficiently low such that the early stage bivalves continue to respire and ingest potassium. As shown in Example 2, treatment of water with potassium cations of greater than about 20 mg/l preferably at least 30 mg/l, or more preferably at least 40 mg/l is toxic over chronic exposure periods and cause long term mortality of adult mussels. Potassium cation concentrations as low as 40 mg/l were shown to cause significant mortality within two weeks and complete mortality in just over three weeks. Accordingly, in one embodiment the concentration of potassium cations sufficiently high to kill early stage bivalves and sufficiently low such that the early stage bivalves continue to respire and ingest potassium is between 10 mg/l and 150 mg/l. In one embodiment, the concentration of potassium cations is preferably at least 20 mg/l, more preferably at least 30 mg/l and most preferably at least 40 mg/l. Exemplary ranges of potassium cation concentrations include 20 to 80 mg/l and 80 to 140 mg/l.

The potassium cation may be introduced into the service water in different forms. For example, in one embodiment the potassium cation is introduced as a potassium salt such as potassium chloride. Optionally, the potassium cation is stored and/or introduced to the service water system in aqueous form. The potassium cation may also be introduced in the form of a potassium containing mineral, such as potash. For example, in one embodiment the potassium is introduced in the form of potassium mono and divalent salts of phosphoric acid. In one embodiment, the potassium is introduced in the form of potassium phosphate, dipotassium hydrogen phosphate (phosphoric acid potassium salt), or monopotassium phosphonate. In one embodiment, the potassium is introduced in the form of potassium sulfate, or sulfate of potash. In one embodiment, the potassium is introduced in the form of potassium bromide. Optionally, potassium is introduced along with an oxidizer, such as in the form of potassium permanganate. Preferably the potassium is introduced in a form which is non-toxic or sparingly toxic to other species such as trout or daphnia.

In one embodiment, the method comprises maintaining a concentration steady state concentration of potassium cation in the service water of the service water system for 2 to 30 days, or any range there between. Preferably, the range is from 2 to 14 days and may be 3 to 10 days, 10 to 14 days, 5 to 10 days, or 8 to 12 days. In one embodiment, the duration of treatment with potassium cation depends on the temperature of the water. Bivalves in bodies of water at lower temperatures generally require longer treatment times to control growth of the population than bivalves in warmer water. For example, when the water temperature is less than about 15° Celsius, bivalves uptake potassium cations much more slowly, which extends the time required to achieve complete mortality. In one embodiment, the range is from 10 to 30 days, from 14 to 30 days, from 14 to 25 days, from 20 to 30 days or from 14 to 20 days.

Various methods known in the art are useful for maintaining a steady state concentration of potassium cations in the service water of the service water system. For example, in one embodiment the volume of the service water system is used to determine an amount of potassium cation to be introduced into the system to obtain the desired concentration of potassium cation. In one embodiment, the potassium cation concentration is analyzed in the service water system and the method includes increasing or decreasing the amount of potassium cation introduced into the service water in order to obtain and maintain the desired concentration.

A skilled person will appreciate that introducing potassium cations into a static or semi-static service water system will not necessarily dissipate the potassium cations within the entire volume of the service water such that the concentration of potassium cations within the service water in the service water system is evenly distributed. Accordingly, in one embodiment the service water in the service water system is circulated or let to flow from an inlet to an outlet during or after the introduction of potassium cations into the service water system and then terminating the flow of the service water. This has the advantage of circulating and dissipating the potassium cations introduced to the service water system in order to reach areas in the service water system that may contain settlement stage mussels.

For example, in one embodiment prior to addition of potassium cations to the system, as assessment may be done to determine which areas are susceptible to colonization. Dissolved oxygen data may be collected at various points throughout a system and filtered water samples analysed for the presence and mortality of free-floating mussel larvae in various sections of the distribution piping to help identify areas of mussel colonization.

Approximate volumes of sitting water may then be calculated to determine amounts of potassium cations required for the specific static or semi-static service water system. Optionally, in one embodiment a valve manipulation strategy is designed based on system drawings and/or site information in order to route water through the system with minimal disruption of normal operations while still reaching all target areas.

For example, in one embodiment a potassium cation feed solution, (e.g. 20 wt % aqueous KCl) is metered to the water system using a positive displacement dosing pump with calibration columns, relief valves, fittings and appurtenances. A predetermined flow is induced at the system extremities through the operation of fire hydrants and/or other bleed or control valves, and feed solution is added to the system until the target concentration is attained. Discrete grab samples may be collected at locations downstream of the introduction of potassium cations, and analysed to determine the concentration of $K^+$ in the water using a portable cation specific probe. The chemical dosing pump flow rate may be varied as a result of the measured concentrations to ensure the target steady state concentration is obtained and/or maintained within the service water in the service water system.

Optionally, once the target concentration of potassium cation is detected in all areas of concern, the addition of potassium cation to the system is turned off, e.g., the flow of water through the system may be stopped. The isolated system is left for a treatment period of at least two (2) to thirty (30) days to ensure sufficient mortality of the target organisms, depending on the water temperature and system layout. In one embodiment, the service water is discharged from the service water system at the end of the 2 to 30 days. In one embodiment, this helps remove any settlement stage mussels suspended in the service water and/or shell debris from the service water system.

In one embodiment, water samples may be collected at various locations throughout the system shortly after the chemical dosing operation has been stopped to determine if any leakage of service water is occurring within the system and ensure there is not any continuous depletion of potassium cation concentration in the system during the treatment period. If it is determined that leakage is occurring, potassium injection may be resumed at low levels on a continuous basis to ensure adequate steady state concentrations of potassium are maintained during the treatment period.

As set out herein, samples may be taken from one or more positions within the service water system during or after treatment to ensure that the potassium cation concentrations are at the desired levels within the service water system. For example, in one embodiment one or more potassium analyzers is used to monitor potassium cation levels in the service water system. Preferably, the potassium analyzers are downstream of sites where potassium cation is introduced into the service water system. In one embodiment, the potassium analyzer is a portable potassium cation probe. Optionally, the samples are sent to external laboratories for testing and/or verification of potassium cation concentrations.

In one embodiment, during the treatment period a signal from the analyzer is transmitted to a controller, such as a programmable logic controller (PLC) which compares the analyzer value to a pre-determined set point. The controller is optionally connected back to one or more devices such as a portable injection system for introducing potassium cations into the service water. In one embodiment, the controller then increases or decreases the amount or rate of introduction of potassium cations to obtain and/or maintain the target potassium cation concentration. Optionally, the introduction of potassium cations into the service water system can be manually adjusted based on data from a potassium analyzer or from monitoring a live colony of bivalves.

In one embodiment, additional potassium analyzers, which may be interfaced with a recording device, such as circular paper chart recorders or electronic data loggers, at various sites in the service water system so that dosing trends can be tracked throughout critical areas of a given plant facility. The recorded data may be used to monitor the levels of potassium cations cation in the service water system over time. In one embodiment, the recorded data is useful for ensuring compliance with environmental regulations and/or ensuring that a predetermined level of potassium cations are maintained in the service water system over time, such as during the treatment period In one embodiment, potassium cations are introduced at one or more locations in the service water system. For example, in one embodiment existing access points or ducts in fluid communication with the service water system may be used to introduce potassium cations into the service water system. Preferably, at least one of the locations is at or near the water supply inlet from the body of water.

In one embodiment, potassium cations are introduced to the service water system using one or more injections systems. Preferably, the injection system is or comprises a portable injection system. Accordingly, when treatment is required, the injection system may be brought to the plant, such as in a truck or a trailer and, upon completion of a treatment cycle, the truck or trailer may be optionally removed from the plant.

The injection system may comprise a storage container for the source of the potassium cations and a dosing system for continuously or periodically injecting potassium cations into the service water. The injection system preferably also includes one or more analyzers for monitoring the concentration of potassium cations in the service water.

If the potassium cations are introduced into the service water in the form of potassium chloride, then the container may be any suitable storage container for the solid or liquid compound. The container may be a portable spill storage tank, such as a polyethylene storage tank. Storage tank sizes may vary with the scope of the method and are preferably sized to contain 130% of the expected reagent that will be required but may be smaller and may be refilled or replaced from time to time during a treatment cycle.

The dosing system may be any suitable equipment for delivering a predetermined quantity of the potassium cation into the service water. In one embodiment, the dosing system for introducing potassium cation into the water system comprises a diaphragmatic metering pump, a peristaltic pump, positive displacement pump, gravity feed, an education device, such as a Venturi injector or any delivery device suitable for metering and/or delivering potassium cation into the service water.

In one embodiment, the methods described herein include monitoring one or more live colonies of the bivalves in the service water of the service water system (e.g., a colony placed in a container in the service water wherein the container permits the flow of service water into and out of the container such that the water in the container is comparable to that of the service water at that location in the system) or under conditions comparable to those in the service water (e.g., conditions that are comparable to those in the service water with respect to potassium cation concentrations and temperature). Accordingly, one or more observation tanks containing a live colony may be provided in the truck or trailer. The tank is filled with water that is either drawn from the treated service water or which is separately treated to mimic the conditions of the treated system water. The colony may be drawn from the service water or the body of water. The monitoring of the live colony may be used to determine when to terminate treatment. For example, treatment of the service water with potassium cation may be terminated when a desired reduction in colony number or death of a live colony is observed in the observation tank or a set time after the desired reduction or death is observed. FIG. 1 shows one embodiment of a water permeable container (10) seeded with a live colony of bivalves (20).

Monitoring a live colony of bivalves in the service water of the service water system, or under comparable conditions, provides a number of advantages. In one embodiment, monitoring a live colony of bivalves allows for the system operator to gauge the success of the treatment and to make changes to the treatment conditions or duration of the treatment. Accordingly, the observation tank may be used to control the treatment or as a back-up to check that predetermined treatment conditions are successful. Accordingly, terminating treatment when the observed live colony of bivalves is killed or reduced to acceptable levels prevents discontinuing treatment too early before the desired level of control or eradication of the bivalves is achieved. Furthermore, terminating treatment when the live colony of bivalves is killed or reduced to acceptable levels prevents overtreating the service water system and the discharge of unnecessary amounts of potassium cations.

Different positions in a service water system may experience different conditions with respect to temperature and/or variations in potassium cation levels. Therefore, instead of using a single observation tank or observing a contained colony in one location of the service water system, a plurality of live colonies of bivalves may be placed and monitored at different positions in the service water system or in a plurality of tanks mimicking the conditions at different locations in the service water system. Accordingly, in one embodiment monitoring one or more live colonies of bivalves at different positions within the service water system, or under comparable conditions, permits the success of the treatment to be monitored throughout the service water system.

It will be appreciated that a colony of bivalves that is already present in the service water system or which is seeded in the service water may be monitored during treatment of the service water in the service water system. Alternately, a live specimen bioassay seeded with bivalves may be monitored (such as in an observation tank) under comparable conditions.

For example, in one embodiment the methods described herein include seeding a water permeable container with a sample of live bivalves. In one embodiment, colonies of live adult mussels are placed in a container comprising a mesh bioassay basket and are placed at the system extremities to assess the effectiveness of the treatment. Preferably, the sample of bivalves is first acclimatized to ambient conditions of the service water. For example, the sample of bivalves may be placed in untreated water for at least 24 hours prior to placing the sample of bivalves in the service water of the service water system or service water with potassium cation concentrations and temperatures comparable to those in the service water system. Accordingly, the container may be placed in the service water of the service water system or the live colony may be placed in an observation tank having water that has potassium cation concentrations and temperatures comparable to those in the service water system. The viability of the bivalves may be determined, such as by determining the number of live bivalves in the container or observation tank. Bivalve mortality is correlated with the effectiveness of the treatment. For example, the mortality of the bivalves that are being monitored may be used to modify and/or terminate the treatment of the service water. In one embodiment if the bivalves that are being monitored are killed, the treatment of the service water is terminated. In one embodiment, if the bivalves that are being monitored are not killed within a specific time period following the start of treatment, such as 1 day, 2 days 3 days, 5 days, 10 days or 15 days, the amount of potassium cation introduced into service water of the service water system may be increased.

The bivalves may be monitored at least once during the treatment of the service water system. Preferably, the bivalves are monitored periodically such as every 12 hours, every day, every 2 days, every 3 days, every 4 days, every 5 days, every 6 days or every 7 days, or combination thereof, during the treatment. Optionally, the bivalves are monitored periodically after 2 days of treatment, after 4 days of treatment, or after 7 days of treatment.

Bivalve mortality can readily be monitored and determined using methods known in the art. For example, bivalve mortality may be determined by a lack of response of the bivalve to gentle prodding, by physical features such as the presence of a gapped open shell or the like.

In one aspect of the invention, the inventors have determined that bivalves treated with potassium show signs of potassium intoxication such that it is difficult to assess whether the bivalves are dead or merely showing signs of toxicity from which they may recover. In one embodiment, mussel mortality is assessed by identifying at least one bivalve which is showing signs of potassium intoxication and removing it from the container; exposing the removed bivalve to untreated flowing water; and classifying the bivalve as dead if the bivalve does not recover after at least 24 hours in the untreated water. In one embodiment, the method involves classifying the bivalve as dead if the bivalve does not recover after at least 48 hours in the untreated water. Recovery of the bivalve may be determined by a positive response of the bivalve to gentle prodding.

For example, in one embodiment mussels showing signs of potassium intoxication are removed from the containers in groups of ten and are placed in recovery chambers containing untreated flowing water. Optionally, latent mortalities are determined at 24 hour and/or 48 hour durations. Total mortality (100%) of mussels is determined to have been reached when no mussel recovery is observed after 48 hours. In one embodiment, treatment of the service water system with potassium cations is terminated when bivalve mortality reaches a predetermined threshold, such as greater than or equal to 80%, 90%, 95% or 100% mortality.

As used herein, a "colony" refers to two or more bivalves, preferably 10 or more, 50 or more, about 100 bivalves or greater than about 100 bivalves. Preferably, a statistically significant number is used. In one embodiment, the colony is a colony of zebra mussels and/or or quagga mussels. In one embodiment, the colony is attached to a surface. Optionally, the colony includes one or more settlement stage mussels and preferably essentially comprises such mussels.

Optionally, compliance sampling at designated service water system effluent site(s) is completed to verify that potassium is not entering the receiving water body at higher than expected concentrations that other required effluent parameters are within acceptable limits. In one embodiment, the methods described herein further include demonstrating compliance in effluent water through the collection and analysis of grab samples.

The following non-limiting examples are illustrative of the present disclosure.

EXAMPLE 1

Effect of Potassium Levels on Adult Zebra Mussels

Laboratory research was carried out to investigate potash for mussel control by itself or in combination with oxidizing agents such as chlorine or hydrogen peroxide. The addition of potassium chloride (KCl) and elevated water temperatures proved to be effective for increasing the efficacy of all treatment options. Surprisingly, while the addition of potassium as KCl significantly reduced treatment time for all protocols, KCl in combination with slightly increased temperatures was as or more effective than any of the combinations tested.

Experimental Protocols and Results

Experiments were carried out with adult zebra mussels using potassium chloride (KCl) alone, as well as chloramine, hydrogen peroxide and combinations thereof to determine the estimated time to 95% mortality. Experimentation was carried out at 100 mg/L $K^+$ and test temperatures ranged from 2 to 30° C.

TABLE 1

Estimated time (hours) to 95% mortality for various chemical combinations (all KCl experiments at 100 mg/L $K^+$, *indicates extrapolated value)

| Conditions | Temperature (° C.) | | | | | |
|---|---|---|---|---|---|---|
| | 10-12 | 12-14 | 13-17 | 20-21 | 22-24 | 14-26 |
| KCl alone | 283* | 165 | 113 | 56 | 33* | 22 |
| chloramine 2.0 mg/L | | | 87 | | | |
| chloramine 1.0 mg/L | 258 | | 209 | | | 60 |
| chloramine 0.5 mg/L | 480* | | | | | 97* |
| KCl/2.0 mg/L chloramine (pre-exposure) | | | 38 | | | |
| KCl/1.0 mg/L chloramine (pre-exposure) | 35 | | 86 | | | 16 |
| KCl/0.5 mg/L chloramine | 56 | | | | | 21 |
| KCl/1.0 mg/L chloramine | 40 | | 50 | | | 19 |
| $H_2O_2$ 10 mg/L | | 227 | | 36 | 21 | |
| $H_2O_2$ 5 mg/L | | 1714* | | 455* | 294* | |
| KCl/10 mg/L $H_2O_2$ (pre-exposure) | | 104 | | 38 | 32* | |
| KCl/5 mg/L $H_2O_2$ (pre-exposure) | | 128* | | 53* | 34* | |
| KCl/10 mg/L $H_2O_2$ (simultaneous) | | 75 | | 29* | <12 | |

At water temperatures ranging from 14 to 26° C., 100 mg/L of potassium cation resulted in 95% mortality in less than 1 day (22 hours) significantly less time that was required to achieve 95% mortality with 1.0 mg/L chloramine (60 hours).

EXAMPLE 2

Effect of Low Levels of Potassium Cations on Veligers and Adult Zebra Mussels

Mortality studies using flow through contact chambers were performed with young adult (<1.5 cm) zebra mussels and naturally occurring veliger populations at a small tributary of a canal located in southern Ontario, Canada. Water temperatures ranged between 20 and 25° C. throughout the trial.

Adult zebra mussels were exposed to three concentrations of $K^+$ (40 mg/l, 30 mg/l, and 20 mg/l) as well as a control chamber. Each concentration as well as the control was replicated three times. The nature of the design allowed for simultaneous trials with adults and veligers. Sixty adult mussels (six groups of ten) were exposed in each replicate test concentration and control tank. Mussels were contained in PVC mesh baskets which allowed free flow of water while maintaining the mussels in discrete groups of ten.

In addition to adult trials, six PVC settling plates were installed in one replicate tank at each test concentration as well as the control. The presence of naturally occurring veliger larvae in the water source provided the opportunity of determining settling rates at each test concentration.

A concentrated potassium solution was metered into each replicate test line prior to its entering the test tanks from a pre-mixed batch tank. Potassium source was commercial grade potash which was 60% potassium by weight. The potassium concentration was controlled through differential metering rates. Flow-through trials were carried out for 52 days at which point final mortality in adults was recorded.

Results

Mortality was observed at all three test concentrations. No mortality was observed in control tanks. Complete mortality of adult mussels was observed within 25 days in all 40 mg/l test tanks. Final mortality in 30 mg/l and 20 mg/l tanks were 91% and 73% respectively at the end of the 52 day trial.

Very low level larval settlement was observed at 20 mg/l. Densities ranged from 22 to 65 mussels/m². No larval settlement was detected on plates exposed to 30 mg/l or 40 mg/l over the 52 day trial period.

Discussion and Conclusions

It is apparent from the results of this trial that even very low concentrations of the potassium cation can be toxic to zebra mussels over chronic exposure periods. Concentrations as low as 20 mg/l can be seen to suppress new mussel settlement as well as cause long term mortality of adult mussels. In addition, potassium concentrations as low as 40 mg/l appear to be acutely toxic, causing significant mortality within two weeks and complete mortality in this trial in just over three weeks.

Therefore, a range of 20-40 mg/l $K^+$ at 100 mg/L potassium chloride as a control agent proves to eradicate mussels over different time periods. Potassium in the form of commercially available potash is therefore an inexpensive and effective means of controlling zebra mussel settlement and growth in fire protection systems or other low or intermittent flow systems that were previously difficult or expensive to treat.

EXAMPLE 3

Toxicity Data for Potassium on Non-Target Species

Studies were performed to investigate the environmental effects on non-target species of treatment with concentrations of potassium effective for controlling zebra mussels. As set out below, potassium when discharged at concentrations of 100 mg/l or less is an environmentally benign method of zebra mussel control. This is an important advantage over other methods of controlling zebra mussels such as by the use of chlorine or other oxidizing agents which can result in significant non-target species toxicity.

Methods

A stock solution at 1000 mg/l KCl was used to set all tests. Dilutions were made from these stocks. Test methods were as dictated by EPS protocols for each test organism.

Results

Results of this study indicated that *Daphnia magna* were most susceptible to potash. In acute tests LC50 values of 188.8 mg/l and 1248.4 mg/l were calculated for *Daphnia magna* and Rainbow trout respectively. Chronic tests showed similar trends indicating a greater effect on invertebrates than on fish species. No effect concentrations (NOEC) of 193 mg/l and 302 mg/l were observed for *Ceriodaphnia* and fathead minnows respectively. A lethal effect concentration (LOEC) of 385 mg/l was detected for *Ceriodaphnia* and 603 mg/l was detected for Rainbow trout as shown in Table 2.

The threshold effect concentration (TEC) which is generally used as a standard measure for environmental consideration was 272.6 mg/l for *Ceriodaphnia* and 426.7 mg/l for fathead minnows. For the organisms that survived in trials, no long term growth or reproductive effect was seen at any concentrations tested.

TABLE 2

| | | | | | | | | | |
|---|---|---|---|---|---|---|---|---|---|
| | | KCl Toxicity Test Results in mg/l. | | | | | | | |
| | | IC50 | IC25 | | | | GROWTH/ | | |
| | LC50 | (95% | (95% | SURVIVAL DATA | | | REPRODUCTIVE DATA | | |
| Test Organism | (95% cl) | CL) | CL) | TEC | NOEC | LOEC | TEC | NOEC | LOEC |
| *Ceriodaphnia dubia* | 219.6 (173.0-279.0) | 256.8 (220.6-277.2) | 189.3 (76.1-228.1) | 272.6 | 193 | 385 | NED | NED | NED |
| *Daphnia Magna* | 188.8 (152.2-234.1) | | | | | | | | |
| Fathead minnow | 512.7 (458.7-567.5) | 892.5 (852.4-904.0) | 736.2 (669.1-753.5) | 426.7 | 302 | 603 | NED | NED | NED |
| Rainbow trout | 1248.4 (1047.6-1487.7) | | | | | | | | |

NED-no effect detected

Discussion and Conclusions

The data presented here confirms that potassium would be useful for the control of zebra mussels in fish hatcheries because of its low toxicity to non-target species. Both Rainbow trout and fathead minnow tests indicated that concentrations of KCl, toxic to zebra mussels, were non-toxic and had no chronic effect on these non-target species even at ten times these concentrations.

While *Daphnia magna* were more sensitive, they were still not affected by concentrations known to be acutely toxic to zebra mussels. When compared to other acutely toxic agents such as non-oxidizing molluscicides, potassium fairs well. In fact, quaternary ammonium compounds have been found to be greater than 100 fold more toxic to *Daphnia magna* than to the target organism (zebra mussels).

The use of commercially available potash for control of zebra mussels in fire protection systems is therefore a cost effective, short duration treatment alternative to other approved treatments. Potassium when discharged at concentrations of 100 mg/l or less is an environmentally benign method of zebra mussel control. While it is unlikely that treatment of static or semi-static service water systems such as fire systems would result in significant discharge of effluent containing the product, it is interesting to know that even full strength concentrations (100 mg/l) would not result in deleterious environmental effects. Higher concentrations could also be safely used given the dilution that would in all likelihood take place.

EXAMPLE 4

Control of Zebra Mussels in a Semi-Static Service Water System for Fire Protection at a Chemical Plant The methods for zebra mussel control described herein using potassium cations were tested in a Fire Protection System (FPS) at a chemical plant. The FPS receives water from a local river through a rock berm that forms the forebay for the plant. Water is drawn from the forebay through travelling screens and sluice gates before entering the wet well beneath the service water pumps. The pressure in the FPS is maintained with river water through the use of a jockey pump at the pumphouse during periods of low firewater use.

The chemical plant has two FPS sites. The Butyl FPS receives water from the self-contained reservoir located on the neighbouring Main site When required, make-up water to the reservoir is supplied by the Main Site pumphouse.

Site Treatments—Main Site

A portable potash injection system was installed inside the River Pumphouse (RPH). Injection rates were manually manipulated to attain appropriate potassium levels throughout the FPS.

Potash was injected into the discharge end of a continuously running firewater booster pump. Select valves were manipulated and hydrants were flushed to control the movement of potash-rich water throughout the FPS.

Potash solution stored in a 4,540 L (1,200 USG) spill contained polyethylene tank was continuously mixed by a low-pressure pneumatic supply line.

Site Treatments—Butyl Site

The potash injection system provided by ASI was installed at the Main site pumphouse facility. Injection rates were manually controlled to attain appropriate potassium levels throughout the FPS.

Potash was injected into the discharge end of the firewater pump at the Main site pumphouse and select valves were manipulated to move the potash-rich water through the FPS in a controlled manner. Hydrants were also strategically flushed to circulate the potash-rich water throughout the FPS.

Potash solution stored outdoors in a 3,028 L (800 USG) polyethylene tank was continuously mixed by an electric powered mixer.

During treatments at both the Main site and Butyl site, grab samples were collected to determine potassium levels throughout the FPS.

Bioassay

Bioassays were conducted to monitor the effectiveness of the potash treatment at eradicating mussels from the FPS. Once an adequate level of potassium was achieved in the FPS, one hundred adult mussels contained in a mesh bioassay basket were placed in bioboxes at different positions at the Main Site and at single position at the Butyl site.

Twenty-four hours after seeding the bioboxes, ten mussels that exhibited signs of potassium intoxication (gaping and non-response to probing) were removed ("pulled") from each bioassay and placed in the recovery biobox in a clearly labelled container.

Both recovery bioboxes received untreated river water. The mussels were inspected for latent mortality after 24 hours in recovery and for actual mortality at 48 hours. It was determined during experiments with adult mussels exposed to potassium that adult mussels can recover from potassium intoxication after 24 hours in untreated water; therefore, it is necessary to examine the mussels after 48 hours in recovery. If mussels have not recovered after 48 hours in untreated water, then the mussels will not recover and are declared dead.

Mussels continued to be pulled from the bioassays and placed in the recovery biobox every 24 hours until complete actual mortality was observed in mussels that were in recovery for 48 hours. Water temperature readings were also collected during the treatment.

The purpose of the bioassays was to simulate conditions within the FPS and provide an indication of when mussels succumb to the treatment. Complete mortality in bioassays is indicative of the success of the treatment at eradicating mussels from the FPS. This ensures that the treatment of the service water effectively eradicates the mussels from the service water system and furthermore that the service water is not over-treated with potassium, thereby reducing the amount of potassium required and the amount of potassium released as effluent from the service water system.

Treatment Analysis

Potash treatments were observed to be generally effective in achieving complete mortality in mussels within four (4) to five (5) days of exposure to lethal levels of potassium. Total mussel mortality was observed in bioassays exposed to potash for one day at two separate locations in the FPS (once the system was re-charged) and for two days at a third location downstream of the injection system.

The results from this treatment highlight the importance of restricting usage of the FPS during a potash treatment in order to ensure that the necessary concentrations of potassium are obtained throughout the service water system. Potash treatments are not suitable for flow-through systems, due to the increased amount of chemical required to maintain the lethal concentration (>100 mg/L) required to eradicate mussels, hence why potash is used to treat static FPS.

CONCLUSIONS

Bioassay results from the FPS potash treatments of the Main and Butyl II sites at the chemical plant indicate that the potash treatment was successful at eradicating mussels from the FPS. Annual treatment of the FPS with potassium cations has been effective for controlling the growth of bivalves.

It will be appreciated that certain features of the invention, which are, for clarity, described in the context of separate embodiments or separate aspects, may also be provided in combination in a single embodiment. Conversely, various features of the invention, which are, for brevity, described in the context of a single embodiment or aspect, may also be provided separately or in any suitable sub-combination.

Although the invention has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

The invention claimed is:

1. A method for controlling bivalve growth in a static or semi-static service water system wherein service water is drawn occasionally from a body of water and introduced into the service water system, the method comprising:
   a. monitoring the body of water for the presence of veligers and/or pediveligers;
   b. when an increase in the concentration of veligers and/or pediveligers is detected, introducing potassium cations into the service water system to obtain a steady state potassium cation concentration of 10 to 60 mg/l; and,
   c. maintaining the steady state concentration of potassium cation in the service water for at least 2 to 30 days.

2. The method of claim 1, wherein step a. comprises monitoring the body of water for the presence of pediveligers and step b. comprises introducing potassium cations into the service water system after an increase in the concentration of pediveligers is detected.

3. The method of claim 1, further comprising monitoring a live colony of the bivalves in the service water of the service water system or under potassium cation concentrations and temperatures comparable to those in the service water system and terminating treatment after the bivalves in the live colony die.

4. The method of claim 1, wherein potassium cation is introduced in the form of potassium chloride.

5. The method of claim 4, wherein the potassium chloride is aqueous potassium chloride.

6. The method of claim 1, wherein step (b) comprises flowing the service water through the service water system from an inlet to an outlet to obtain the concentration of potassium cation in the service water in the service water system and then terminating the flow of the service water.

7. The method of claim 6, wherein the service water is discharged from the service water system at the end of the 2 to 30 days.

8. The method of claim 1, wherein the method further comprises analyzing the potassium cation concentration in the service water and increasing or decreasing the amount of potassium cation introduced into the service water in order to maintain the steady state concentration.

9. The method of claim 1, wherein the method further comprises assessing the effectiveness of the potassium cation for controlling bivalve growth in the service water system by:
   d. seeding a water permeable container with a sample of live bivalves;
   e. placing the container in the service water or in water that has potassium cation concentrations and temperatures comparable to those in the service water system; and
   f. determining the viability of bivalves in the container, wherein bivalve mortality is correlated with the effectiveness of the treatment.

10. The method of claim 9, wherein bivalve mortality is assessed by:
   g. identifying at least one bivalve which is showing signs of potassium intoxication and removing it from the container;
   h. exposing the removed bivalve to untreated flowing water; and
   i. classifying the bivalve as dead if the bivalve does not recover after at least 24 hours in the untreated water.

11. The method of claim 1, wherein the method is performed once a year.

12. The method of claim 1, wherein the method is performed only in spring after an increase in the concentration of veligers is detected.

13. The method of claim 1, wherein the method is performed only in fall after an increase in the concentration of pediveligers.

14. The method of claim 2, wherein the method is performed in the fall after an increase in the concentration of pediveligers is detected.

15. The method of claim 1, wherein the method is performed in spring after an increase in the concentration of veligers is detected and in fall after an increase in the concentration of pediveligers is detected.

16. A method for preventing the settlement and translocation of veligers and/or settlement stage bivalves in a static or semi-static service water system wherein service water is drawn occasionally from a body of water and introduced into the service water system, the method comprising:
   a. introducing potassium cation into the service water of the service water system to obtain a steady state potassium cation concentration of 10 to 40 mg/l; and,
   b. maintaining the concentration of potassium cation in the service water of the service water system for 2 to 30 days.

17. The method of claim 16, wherein potassium cation is introduced in the form of potassium chloride.

18. The method of claim 17, wherein the potassium chloride is aqueous potassium chloride.

19. The method of claim 16, wherein step a. comprises flowing water through the service water system from an inlet to an outlet to obtain the concentration of potassium cation in the service water in the service water system and then terminating the flow of the service water.

20. The method of claim 16, wherein the water is discharged from the service water system at the end of the 2 to 30 days.

21. The method of claim 16, wherein the method further comprises analyzing the potassium cation concentration in the service water and increasing or decreasing the amount of potassium cation introduced into the service water in order to maintain the concentration.

22. The method of claim 16, wherein the method is performed once a year.

23. The method of claim 16, wherein the method is performed in the fall.

24. The method of claim 16, wherein the method is performed only in spring after an increase in the concentration of veligers is detected.

25. The method of claim 16, wherein the method is performed only in fall after an increase in the concentration of pediveligers is detected.

26. The method of claim 16, wherein the method is performed in the spring after an increase in the concentration of veligers in the body of water and in the fall after an increase in the concentration of pediveligers in the body of water is detected.

* * * * *